(12) United States Patent  (10) Patent No.: US 8,770,031 B2
Brady                      (45) Date of Patent:     Jul. 8, 2014

(54) CAPACITIVE ACOUSTIC INSPECTION APPARATUS

(75) Inventor: Steven Kenneth Brady, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 601 days.

(21) Appl. No.: 11/839,118

(22) Filed: Aug. 15, 2007

(65) Prior Publication Data

US 2009/0044627 A1    Feb. 19, 2009

(51) Int. Cl.
*G01N 29/04*    (2006.01)

(52) U.S. Cl.
USPC .......................................................... 73/643

(58) Field of Classification Search
USPC .......................................................... 73/643
See application file for complete search history.

(56) References Cited

U.S. PATENT DOCUMENTS

| | | | |
|---|---|---|---|
| 3,577,774 A * | 5/1971 | Steffens et al. | 73/597 |
| 3,604,251 A | 9/1971 | Dixon | |
| 4,085,297 A | 4/1978 | Paglia | |
| 4,439,641 A | 3/1984 | Paglia | |
| 5,608,691 A | 3/1997 | MacLauchlan et al. | |
| 6,584,848 B1 | 7/2003 | Yost et al. | |
| 2007/0164632 A1* | 7/2007 | Adachi et al. | 310/311 |

FOREIGN PATENT DOCUMENTS

| WO | 03073093 A | 4/2003 |
|---|---|---|
| WO | 2007058056 A | 5/2007 |

OTHER PUBLICATIONS

Daimond et al., "Electrostatic-capacitive imaging—a new NDE technique," 33rd QNDE Conference, Portland, Oregon, Jul. 30-Aug. 4, 2006.*
J. Szilard, "Electrostatic coupling" in Ultrasonic Testing, John Wiley & Sons, New York, 1982, pp. 395-399.*
Schindel eet al., "Capacitive and piezoelectric air-coupled transducers for resonant ultrasonic inspection", Ultrasonics, IPC Science and Technology Press Ltd., Guildford GB, vol. 34, No. 6, Aug. 1996, pp. 621-627.
Diamond et al., "A New Capacitive Imaging Technique for NDT", ECNDT 2006, 9th European Conference on NDT, Sep. 2006, Berlin Germany, pp. 1-8.
Dixon et al., A Laser-EMAT System for Ultrasonic Weld Inspection, Ultrasonics, vol. 37, No. 4, Apr. 1999, pp. 273-281.
Krautkramer et al., "Ultrasonic Testing of Materials", 4th Fully Revised Edition, 1990, 3 pages.

* cited by examiner

*Primary Examiner* — John Chapman, Jr.
(74) *Attorney, Agent, or Firm* — Yee & Associates, P.C.

(57) ABSTRACT

A method and apparatus for non-destructive testing. An embodiment of the present disclosure provides a non-destructive inspection system comprising a capacitive acoustic transducer and a control unit connected to the capacitive transducer.

20 Claims, 6 Drawing Sheets

CAPACITIVE ACOUSTIC INSPECTION APPARATUS

BACKGROUND INFORMATION

1. Field

The present disclosure relates generally to the testing of components and in particular to a method and apparatus for performing non-destructive testing of components. Still more particularly, the present disclosure relates to a method and apparatus for non-destructive testing of components using transducers.

2. Background

Aircraft are being designed and manufactured with greater and greater percentages of composite materials. Some aircraft may have more than fifty percent of its primary structure made from composite materials. Composite materials may be used in aircraft to decrease the weight of the aircraft. This decreased weight may improve payload capacities and fuel efficiencies. Further, composite materials may provide longer service life for various components in an aircraft.

Composite materials may be tough, light-weight materials, created by combining two or more dissimilar components. For example, a composite may include fibers and resins. The fibers and resins may be combined to form a cured composite material.

In particular, key components, such as wings and fuselage skins, may be constructed with composite materials, such as, without limitation, a composite laminate. With more and more critical structures being made of composite laminates, methods and techniques to assure that these components meet quality standards are needed more than ever before.

Porosity may occur during processing to create composite components. Porosity may occur when voids form within a material. Currently, much time, effort, and money may be spent on non-destructive measurement systems designed to detect and quantify the porosity in composite components, such as those made using carbon laminates. These currently used techniques may take advantage of the fact that porosity does not block ultrasound signals but attenuates these signals. By measuring the amount of attenuation that occurs when transmitting an ultrasonic signal into a composite component, an estimate of the degree of porosity may be obtained for correlation with manufacturing specifications.

Many of the non-destructive measurement systems employ ultrasound transducers, which may be physical transducers. These types of transducers may require a coupling agent, such as a gel or liquid between the transducer and the sample. In some cases, using a coupling agent may be undesirable.

An electromagnetic acoustic transduction transducer may be used in these situations. These types of transducers may rely on eddy currents to transmit the vibration between the sample and the probe. This type of transducer, however, may not work well with poorly conducting materials, such as, without limitation, dielectrics found in composite materials. A dielectric may be a material that is highly resistant to the flow of an electric current. These types of material may contain carbon fiber and epoxy, which may not be good conductors.

In this situation, an electromagnetic transducer may be used with one or more conducting loops fixed to the sample to allow acoustic energy to be launched into and received from dielectric samples. These types of electromagnetic acoustic transducers, however, require a direct current magnetic field, which adds weight to the non-destructive measurement system. In using loops, time may be needed to attach the loops to the test sample, take measurements, and then remove the loops. Performing this process for each test sample may increase the time needed to test samples.

Therefore, it would be advantageous to have a method and apparatus for minimizing the need for contact with a component in performing non-destructive testing, which overcomes the problems discussed above.

SUMMARY

The advantageous embodiments provide a method and apparatus for non-destructive testing. An embodiment of the present disclosure provides a non-destructive inspection system comprising a capacitive acoustic transducer and a control unit connected to the capacitive transducer.

Another advantageous embodiment provides a method for testing a sample. Power may be supplied to a capacitive acoustic transducer to form a charged capacitive acoustic transducer. An acoustic wave may be sent into a sample. A response to the acoustic wave may be detected with the isolated charged capacitive acoustic transducer.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The disclosure itself, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
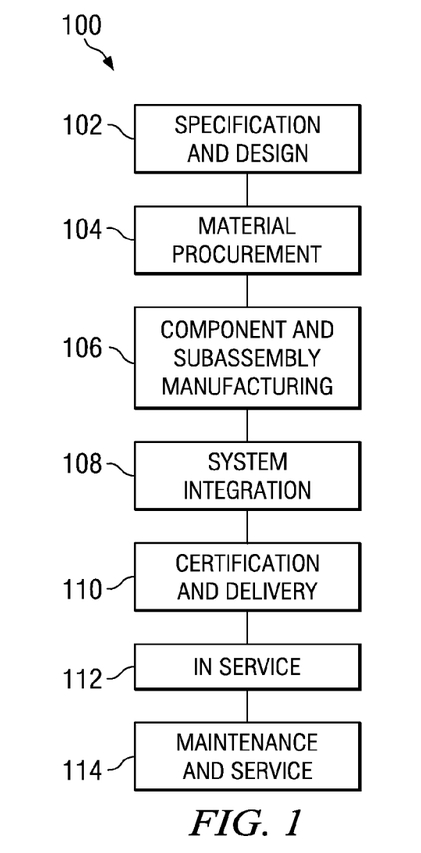
FIG. 1 is an illustration of an aircraft manufacturing and service method in accordance with an advantageous embodiment.
Figure 2:
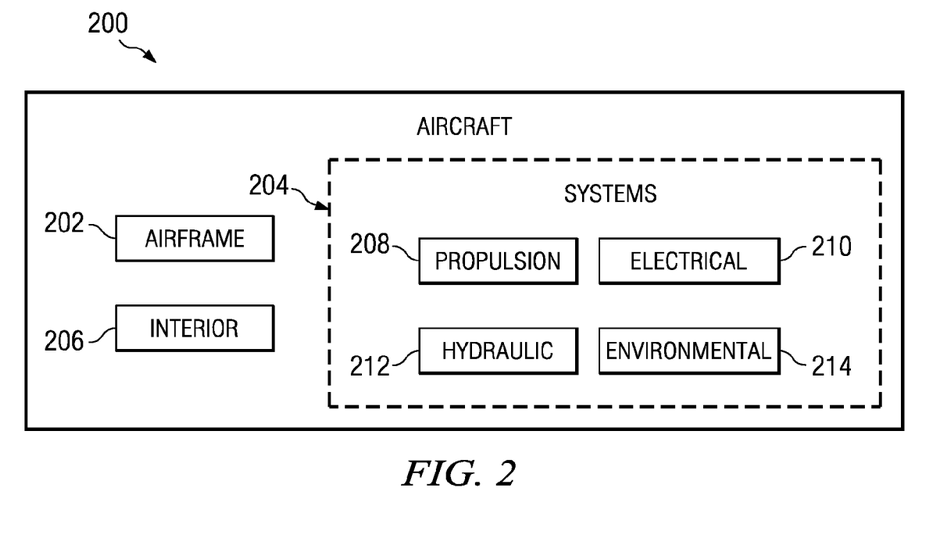
FIG. 2 is an illustration of an aircraft in which an advantageous embodiment may be implemented.

Referring more particularly to the drawings, embodiments of the disclosure may be described in the context of the aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, exemplary aircraft manufacturing and service method 100 may include specification and design 102 of aircraft 200 in FIG. 2 and material procurement 104. During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during any one or more of the stages of aircraft manufacturing and service. For example, components or subassemblies produced in component and subassembly manufacturing 106 in FIG. 1 may be fabricated or manufactured in a manner similar to components or subassemblies produced while aircraft 200 is in service 112 in FIG. 1. Also, one or more apparatus embodiments, method embodiments, or a combination thereof may be utilized during production stages, such as component and subassembly manufacturing 106 and system integration 108 in FIG. 1, for example, by substantially expediting the assembly of or reducing the cost of aircraft 200. Similarly, one or more of apparatus embodiments, method embodiments, or a combination thereof may be utilized while aircraft 200 is in service 112, for example and without limitation, to maintenance and service 114 in FIG. 1.

Figure 3:
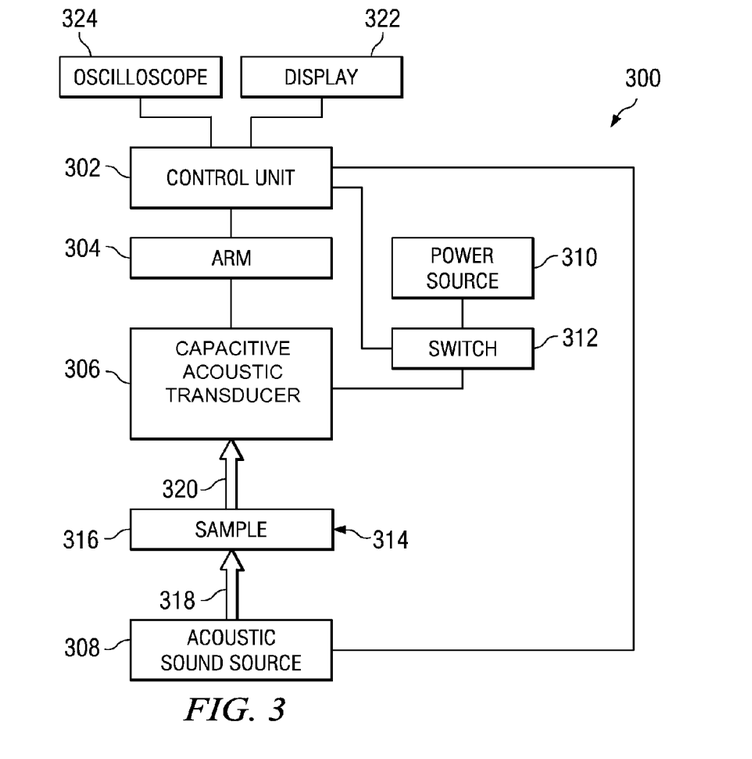
FIG. 3 is an illustration of a non-destructive measurement system in accordance with an advantageous embodiment.

Turning now to FIG. 3, an illustration of a non-destructive measurement system is depicted in accordance with an advantageous embodiment. In this example, non-destructive measurement system 300 may be used to measure acoustic signals transmitted through a material. In particular, non-destructive measurement system 300 may be used to measure signals in poorly conducting or dielectric materials, such as those in composite parts. Non-destructive measurement system 300 may be used to identify porosity levels in these types of materials by measuring the attenuation of signals transmitted in the material. Non-destructive measurement system 300 also may be used to test for other conditions, such as, for example, corrosion or cracking. Non-destructive measurement system 300 includes control unit 302, arm 304, capacitive acoustic transducer 306, acoustic sound source 308, power source 310, and switch 312.

Capacitive acoustic transducer 306 may be mechanically connected to arm 304. Control unit 302 may command arm 304 to move capacitive acoustic transducer 306 to a position close to surface 314 of sample 316. Sample 316 may take various forms. For example, sample 316 may be a composite part, such as a wing panel, a portion of a fuselage, a rudder, or an aileron. Sample 316 may also take other forms, such as, for example, a metal part for an aircraft, parts for other type vehicles, or parts for other structures, such as a dam, power plant, or office building.

Further, capacitive acoustic transducer 306 may be electrically connected to switch 312. Switch 312 also may have connections to power source 310 and control unit 302. In this depicted example, switch 312 may be a two position switch. When switch 312 is in a first position, power source 310 may supply power to capacitive acoustic transducer 306 to charge capacitive acoustic transducer 306. When charged, capacitive acoustic transducer 306 may generate an electric field (not shown).

When in a second position, switch 312 may connect capacitive acoustic transducer 306 to control unit 302. Additionally, capacitive acoustic transducer 306 may be isolated from power source 310. In these examples, switch 312 is depicted as a separate component. Depending on the implementation, switch 312 may be located within control unit 302, or may be part of capacitive acoustic transducer 306, depending on the particular embodiment. Switch 312 may be implemented using different types of switches. For example, without limitation, a contact switch, an actuator, a biased switch, a reed switch, or a toggle switch. Switch 312 may be controlled by a user or by a device, such as control unit 302.

In these examples, without limitation, acoustic sound source 308 may be any device capable of introducing acoustic sound waves into sample 316. For example, a capacitive electromagnetic acoustic transducer, a mechanical transducer, or a laser may be used.

Control unit 302 may send a command to cause acoustic sound source 308 to send signal 318 into sample 316. This signal may propagate through sample 316 to form response 320. Capacitive acoustic transducer 306 may be positioned near or close to surface 314 to detect response 320 without having to contact surface 314.

In operation, control unit 302 may cause switch 312 to switch to a first position, to supply power to capacitive acoustic transducer 306. When sufficiently charged, control unit 302 may cause switch 312 to move to a second position, such that capacitive acoustic transducer 306 may be isolated from power source 310. In this state, capacitive acoustic transducer 306 may generate an electric field. Control unit 302 may monitor the voltage in capacitive acoustic transducer 306 in this state.

Control unit 302 may then send a signal to acoustic sound source 308 to transmit signal 318. Response 320 may cause surface 314 in sample 316 to move or vibrate. If capacitive acoustic transducer 306 is positioned closed enough to surface 314, this movement may cause the electric field to change, which causes the voltage monitored by control unit 302 to change. These changes may be detected by control unit 302 to detect response 320.

Control unit 302 may display these changes on display 322 or through oscilloscope 324. Control unit 302 may be implemented using various devices. For example, control unit 302 may be a computer. Analysis of the results may be performed by control unit 302. For example, control unit 302 may convert the results into porosity levels and provide a comparison of the test results with standards or tolerances for sample 316. Further, control unit 302 may store the results and/or transmit them to a computer for analysis.

In this manner, non-destructive measurement system 300 may detect acoustic waves propagating through different materials, such as those in composite components. Other materials, such as, for example, without limitation, steel, aluminum, metal alloys, plastics, concrete, and glass also may be tested. This detection and launching may be performed without contact with surface 314. This type of feature may be useful when contact with surface 314 is undesirable or infeasible. For example, new steel parts may be too hot to test with methods requiring contact. In this situation, acoustic sound source 308 may be another capacitive acoustic transducer controlled by control unit 302 to generate changes in the electric field. These changes in the electric field can cause movement of the surface to introduce the acoustic wave.

Although capacitive acoustic transducer 306 may be moved using arm 304, arm 304 is not a necessary component for non-destructive measurement system 300. In other advantageous embodiments, capacitive acoustic transducer 306 may be moved by hand. Further, in other embodiments, control unit 302 includes switch 312 and display device, such as display 322 or oscilloscope 324.

Figure 4:
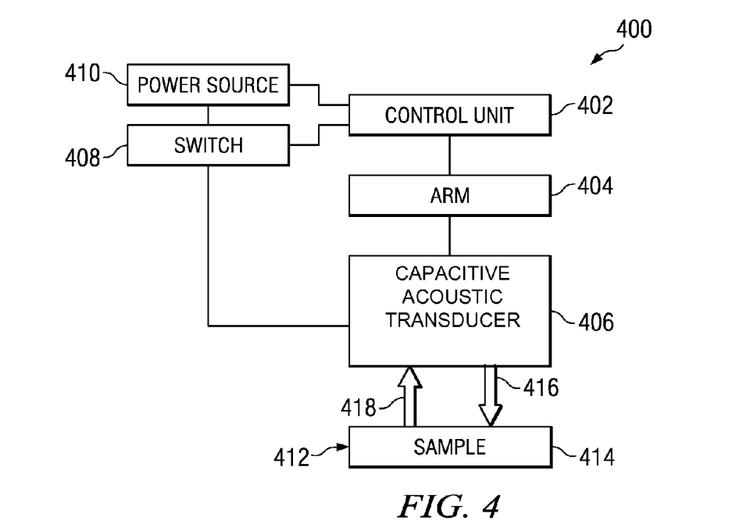
FIG. 4 is a configuration for a non-destructive measurement system in accordance with an advantageous embodiment.

With reference now to FIG. 4, a configuration for a non-destructive measurement system is depicted in accordance with an advantageous embodiment. In this example, non-destructive measurement system 400 includes control unit 402, arm 404, capacitive acoustic transducer 406, switch 408, and power source 410.

Capacitive acoustic transducer 406 is a capacitive acoustic transducer. Capacitive acoustic transducer 406 may be mechanically connected to arm 404. Control unit 402 may command arm 404 to move capacitive acoustic transducer 406 to a position close to surface 412 of sample 414.

Further, capacitive acoustic transducer 406 may be electrically connected to switch 408. Switch 408 also has connections to power source 410 and control unit 402. In this depicted example, switch 408 may be a two position switch. When switch 408 is in a first position, power source 410 may supply power to capacitive acoustic transducer 406 to charge capacitive acoustic transducer 406. When charged, capacitive acoustic transducer 406 may generate an electric field.

When in a second position, switch 408 may connect capacitive acoustic transducer 406 to control unit 402. Additionally, capacitive acoustic transducer 406 may be isolated from power source 410. In these examples, switch 408 is depicted as a separate component. Depending on the implementation, switch 408 may be located within control unit 402 or may be part of capacitive acoustic transducer 406, depending on the particular embodiment.

In this example, capacitive acoustic transducer 406 may transmit acoustic waves and detect acoustic waves. Control unit 402 may be connected to power source 410 to control the supply of power to capacitive acoustic transducer 406 in a manner that causes changes in the electromagnetic field to cause acoustic waves for signal 416 to be generated in sample 414. The power source 410 also may include an alternating current function controlled by control unit 402 to change the electromagnetic field at a frequency, causing oscillations that result in surface 412 moving to generate the acoustic waves.

Control unit 402 then isolates capacitive acoustic transducer 406 from power source 410 using switch 408. Capacitive acoustic transducer 406 detects response 418 through changes in the electric field when surface 412 moves.

Figure 5:
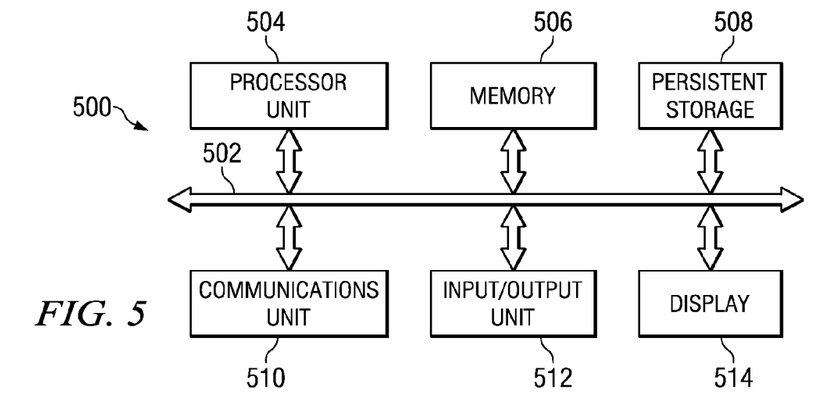
FIG. 5 is an illustration of a data processing system in accordance with an illustrative embodiment.

Turning now to FIG. 5, an illustration of a data processing system is depicted in accordance with an illustrative embodiment. In this illustrative example, data processing system 500 includes communications fabric 502, which may provide communications between processor unit 504, memory 506, persistent storage 508, communications unit 510, input/output (I/O) unit 512, and display 514. Data processing system 500 may be an example of a device used to implement control unit 302 in FIG. 3 and control unit 402 in FIG. 4.

Processor unit 504 may execute instructions for software that may be loaded into memory 506. Processor unit 504 may be a set of one or more processors or may be a multi-processor core, depending on the particular implementation. Further, processor unit 504 may be implemented using one or more heterogeneous processor systems in which a main processor is present with secondary processors on a single chip. As another illustrative example, processor unit 504 may be a symmetric multi-processor system containing multiple processors of the same type.

Memory 506, in these examples, may be, for example, a random access memory. Persistent storage 508 may take various forms depending on the particular implementation. For example, persistent storage 508 may contain one or more components or devices. For example, persistent storage 508 may be, without limitation, a hard drive, a flash memory, a rewritable optical disk, a rewritable magnetic tape, or some combination of the above. The media used by persistent storage 508 also may be removable. For example, a removable hard drive may be used for persistent storage 508.

Communications unit 510, in these examples, provides for communications with other data processing systems or devices. In these examples, communications unit 510 is a network interface card. Communications unit 510 may provide communications through the use of either or both physical and wireless communications links.

Input/output unit 512 allows for input and output of data with other devices that may be connected to data processing system 500. For example, input/output unit 512 may provide a connection for user input through a keyboard and mouse. Further, input/output unit 512 may send output to a printer. Display 514 may display information to a user.

Instructions for the operating system and applications or programs are located on persistent storage 508. These instructions may be loaded into memory 506 for execution by processor unit 504. The processes of the different embodiments may be performed by processor unit 504 using computer implemented instructions, which may be located in a memory, such as memory 506. These instructions are referred to as computer usable program code or computer readable program code that may be read and executed by a processor in processor unit 504. The computer readable program code may be embodied on different physical or tangible computer readable media, such as memory 506 or persistent storage 508.

The different components illustrated for data processing system 500 are not meant to provide architectural limitations to the manner in which different embodiments may be implemented. The different illustrative embodiments may be implemented in a data processing system including components in addition to or in place of those illustrated for data processing system 500. Other components shown in FIG. 5 can be varied from the illustrative examples shown.

For example, a bus system may be used to implement communications fabric 502 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 506 or a cache such as found in an interface and memory controller hub that may be present in communications fabric 502.

Figure 6:
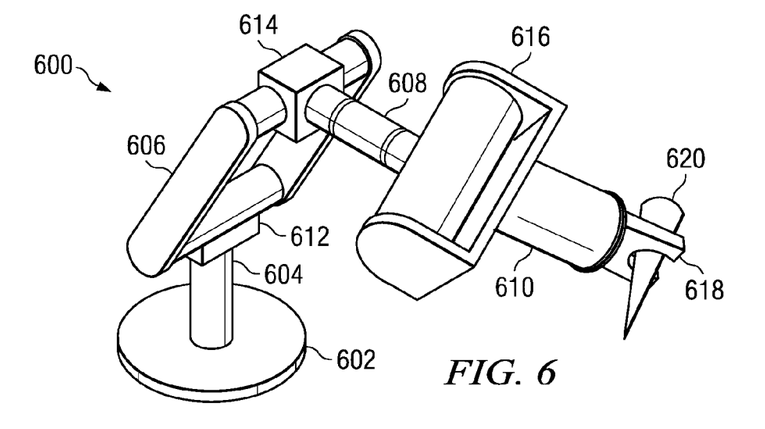
FIG. 6 is an illustration of a robotic arm in accordance with an advantageous embodiment.

Turning now to FIG. 6, an illustration of a robotic arm is depicted in accordance with an advantageous embodiment. In this example, arm 600 is an example of one implementation of arm 304 in FIG. 3 and arm 404 in FIG. 4. In this example, probe arm 600 may include base 602. Support rod 604 may be attached to base 602. Probe arm 600 also may include support member 606, rod 608, and rod 610. These components may be connected to each other by rotary joints 612, 614, and 616. Rod 610 includes clamp 618, which holds capacitive acoustic transducer 620. Capacitive acoustic transducer 620 may be an example of a device, such as capacitive acoustic transducer 306 in FIG. 3 or capacitive electromagnetic acoustic transducer 406 in FIG. 4. These different components form an articulated arm for probe arm 600 that can move probe 620 in three dimensions, including along the X-axis, the Y-axis, and the Z-axis.

Probe arm 600 may include motors (not shown) for moving these components, and circuits (not shown) to receive commands directing the movement. These components may be controlled by commands from a device, such as control unit 402 in FIG. 4. The particular depiction of probe arm 600 is for purposes of illustration and not meant to limit the architecture or design that may be used to implement probe arm 600.

Figure 7:
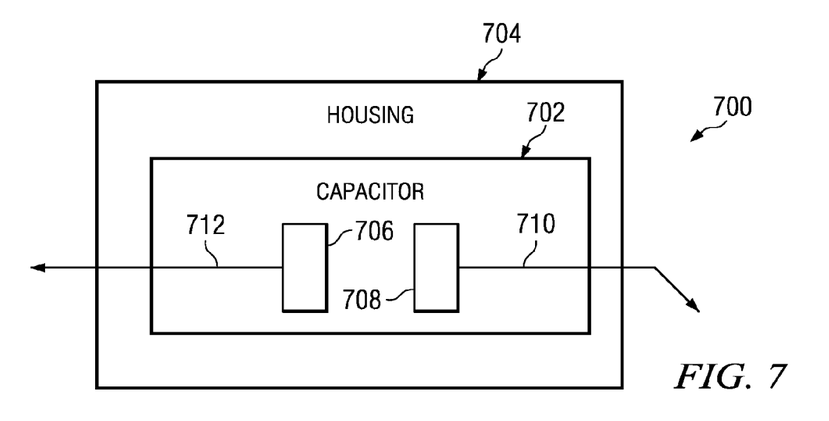
FIG. 7 is an illustration of a capacitive acoustic transducer in accordance with an advantageous embodiment.

With reference now to FIG. 7, an illustration of a capacitive acoustic transducer is depicted in accordance with an advantageous embodiment. In this example, capacitive acoustic transducer 700 is an example of a transducer that may be implemented in probe 306 in FIG. 3 and probe 406 in FIG. 4.

In this example, capacitive acoustic transducer 700 may include capacitor 702 mounted in housing 704. Capacitor 702 may comprise plate 706 and plate 708. Plate 708 may be connected to ground 710, while plate 706 may be connected to power connection 712. Power connection 712 may provide a connection to a power supply.

When power is supplied to power connection 712, capacitor 702 may establish a charge between plates 706 and 708. With this charge, an electric field may be generated by capacitor 702. When capacitive acoustic transducer 700 is positioned close enough to a surface of a test sample, movement in the surface of the test sample may cause changes in the electric field generated by capacitor 702. This change in the electric field may change the voltage between plates 706 and 708. This change in voltage may be measured to detect a response to the transmission of an acoustic signal into the test material.

With respect to detecting a response, the capacitor equation may be:

$$Q = VC \quad (1)$$

where Q is the charge on one plate of the capacitor, V is the voltage across the capacitor, and C is the capacitance of the capacitor. Another equation may be:

$$C = \in A/d \quad (2)$$

where $\in$ is the (absolute) permittivity between plates of a parallel-plate capacitor, A is the area of the plates, d is the separation between the plates, and C is the capacitance of the capacitor. This simplified equation may be used to explain the operation of a surface capacitor that may be used in different embodiments. Absolute permittivity can be expressed in terms of relative permittivity, $\in_r$, and the permittivity of free space, $\in_0$, as $\in = \in_r \in_0$.

Before measurement of an acoustic wave from the sample, the direct current power supply may be used to establish a potential difference between the plates of the capacitor. Before measurement, the capacitor may be isolated from the power supply. When an acoustic wave encounters the surface, that surface may move relative to the nearby surface capacitor. Given that the sample may be $\in_r \neq 1.00$, this may change the capacitance of the surface capacitor as set out in equation (2). As the capacitance changes, equation (1) shows that the voltage across the capacitor may change since the charge is fixed. This time-varying voltage may be a measurement of the acoustic wave.

Further, in these examples, capacitor 702 may be a surface capacitor. Capacitor 702 may be implemented using other types of capacitors, such as a parallel plate capacitor. With a parallel plate capacitor, the sample may be placed between the plates. A surface capacitor, in these examples, may be a capacitor that is substantially flat. In other words, a surface capacitor may be formed on a flat surface, such as a printed circuit board.

Figure 8:
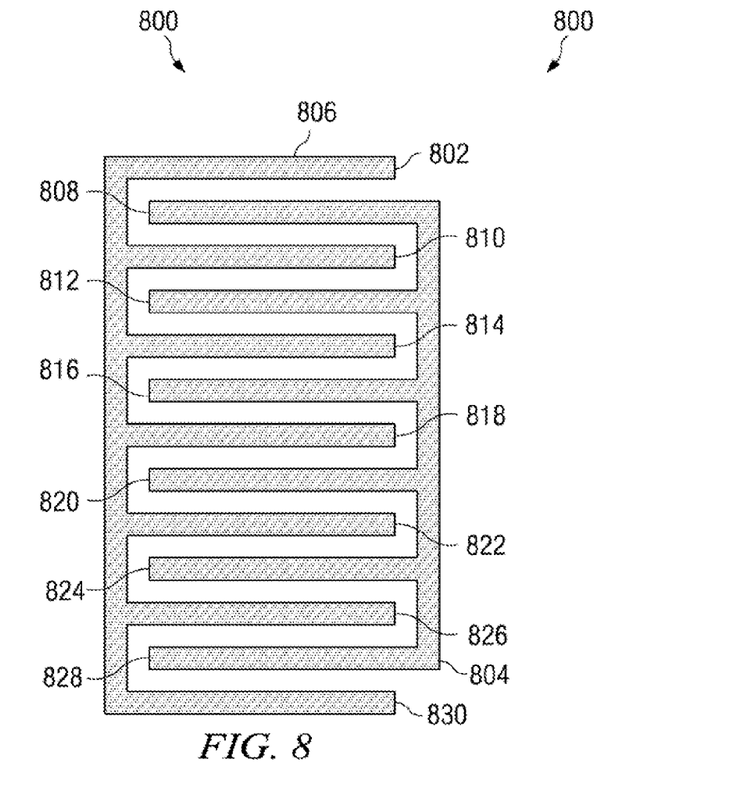
FIG. 8 is an example layout for a capacitor in accordance with an advantageous embodiment.

Turning now to FIG. 8, an example layout for a capacitor is depicted in accordance with an advantageous embodiment. In this example, layout 800 may be for a surface capacitor, such as capacitor 702 in FIG. 7. In this example, layout 800 may be a serpentine or an interlaced layout. Section 802 may represent one side of layout 800 while section 804 may represent the other side of layout 800. Fingers, such as fingers 806, 808, 810, 812, 814, 816, 818, 820, 822, 824, 826, 828, and 830 may be present in layout 800. These fingers may be in an "interlaced" configuration.

Figure 9:
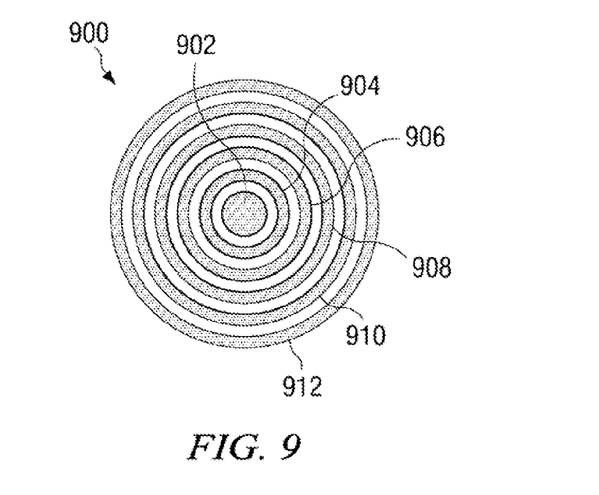
FIG. 9 is an illustration of another layout for a capacitor in accordance with an advantageous embodiment.

Turning now to FIG. 9, an illustration of another layout for a capacitor is depicted in accordance with an advantageous embodiment. In this example, layout 900 may be an example of another layout for a capacitor in a capacitive acoustic transducer, such as capacitive acoustic transducer 700 in FIG. 7.

In this example, layout 900 may include central section 902 and rings 904, 906, 908, 910, and 912. Central section 902, ring 906, and ring 910 may be electrically connected and form one plate in layout 900. Rings 904, 908, and 912 may be grounded to form the other plate in layout 900.

Figure 10:
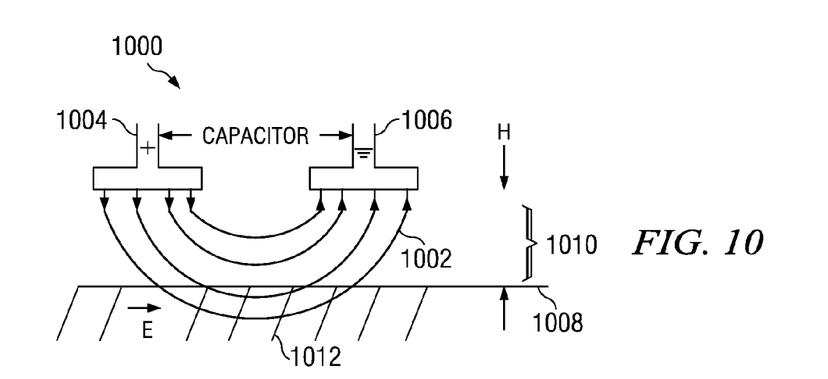
FIGS. 10 and 11 are illustrations of an operation of a capacitive acoustic transducer with a dielectric sample in accordance with an advantageous embodiment.
Figure 11:
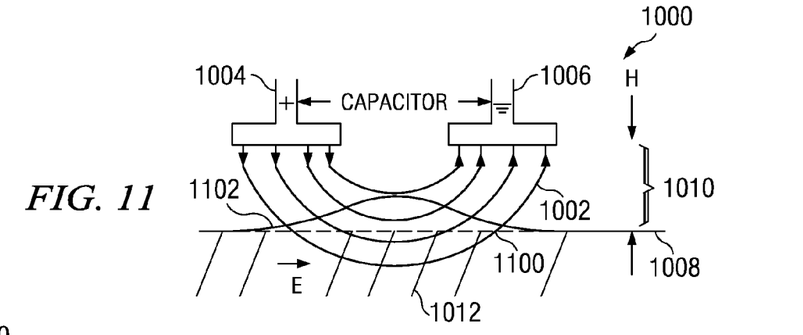

Turning now to FIGS. 10 and 11, illustrations of an operation of a capacitive acoustic transducer with a dielectric sample are depicted in accordance with an advantageous embodiment. In this example, capacitor 1000 generates electric field 1002 when a voltage is established between plates 1004 and 1006. This electric field may extend into surface 1008 of dielectric sample 1012. Plates 1004 and 1006 are positioned distance 1010 from surface 1008.

A signal transmitted into dielectric sample 1012 may cause an acoustic wave to propagate within dielectric sample 1012, which may cause surface 1008 in dielectric sample 1012 to move from position 1100 to position 1102, changing distance 1010 between surface 1008 and capacitor 1000. This movement of surface 1008 may cause a change in electric field 1002. In turn, the change in electric field 1002 may change the voltage across plates 1004 and 1006. This change in voltage may be detected to detect the response to the transmitted signal.

Further, the voltage across capacitor 1000 may be varied to place capacitor 1000 in a transmit mode within the capacitive acoustic transducer. Varying the voltage may change the charge between plates 1004 and 1006 to change electric field 1002. The change may be at a controlled frequency, generating forces in the dielectric sample 1012 that may cause acoustic waves to propagate through dielectric sample 1012.

Figure 12:
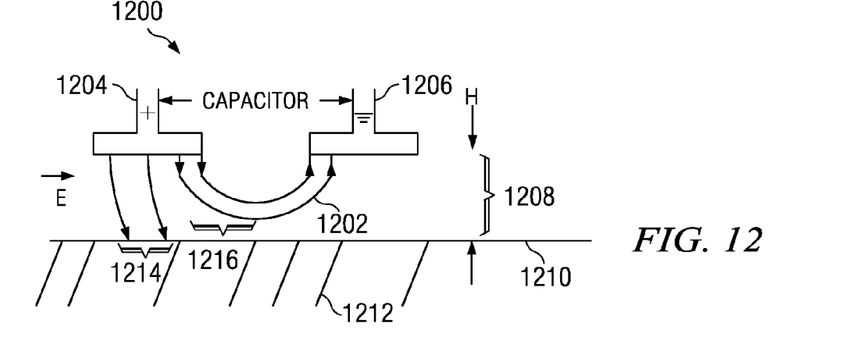
FIGS. 12 and 13 are illustrations of an operation of a capacitive acoustic transducer with a conducting sample in accordance with an advantageous embodiment.
Figure 13:
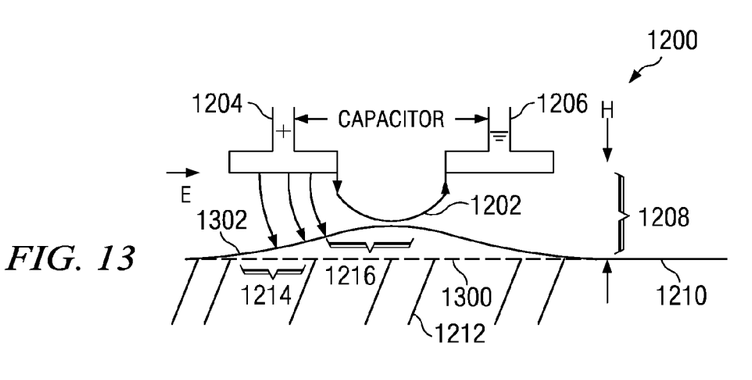

Turning now to FIGS. 12 and 13, illustrations of an operation of a capacitive acoustic transducer with a conducting sample are depicted in accordance with an advantageous embodiment. In this example, capacitor 1200 may be charged such that electric field 1202 is generated by plates 1204 and 1206 in capacitor 1200, which are distance 1208 from surface 1210 of conducting sample 1212. In this example, conducting sample 1212 may be held at ground. As a result, portion 1214 of electric field 1202 shunts to surface 1210 of conducting sample 1212. Portion 1216 terminates on plate 1206 in these examples.

When an acoustic wave travels through conducting sample 1212, surface 1210 may move from position 1300 to position 1302 changing distance 1208 in a manner that causes more of electric field 1202 to terminate on conducting sample 1212. This disturbance in electric field 1202 may be detected to detect the response. In other embodiments, the voltage across plates 1204 and 1206 may be varied to generate ultrasound waves that may be transmitted into conducting sample 1212.

Figure 14:
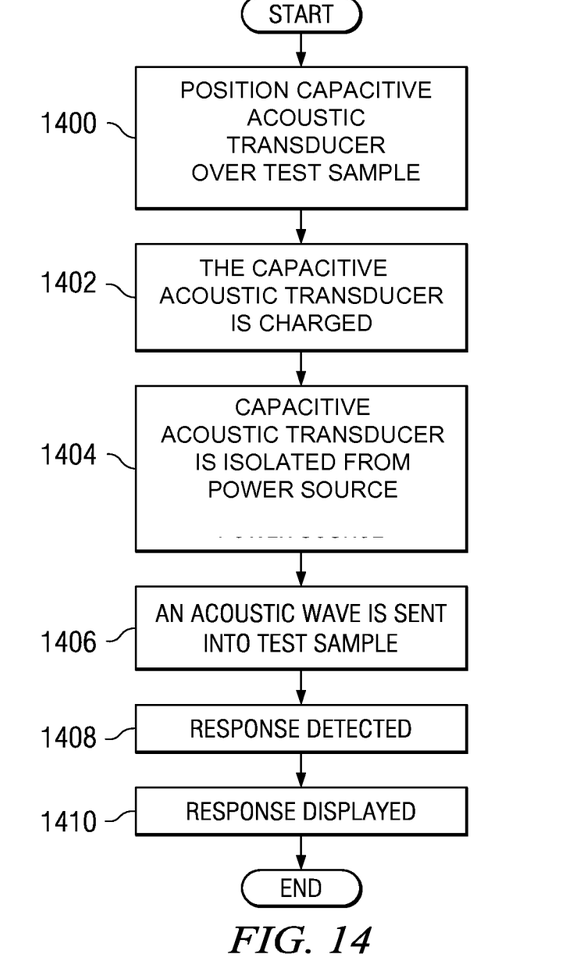
FIG. 14 is a flowchart of a process for testing a sample in accordance with an advantageous embodiment.

Turning now to FIG. 14, a flowchart of a process for testing a sample is depicted in accordance with an advantageous embodiment. The process illustrated in FIG. 14 may be implemented using a non-destructive testing system, such as non-destructive measurement system 300 in FIG. 3 or non-destructive measurement system 400 in FIG. 4.

The process begins by positioning a capacitive acoustic transducer over the test sample (operation 1400). In these examples, the test sample may be, for example and without limitation, a poorly conducting sample, such as a dielectric material or a composite material. The sample also may be a conductor. The capacitive acoustic transducer is charged (operation 1402). In these examples, the capacitive acoustic transducer is charged to some selected level. Thereafter, the process may isolate the capacitive acoustic transducer from the power source (operation 1404).

The isolation may be performed by opening a switch in a connection between the capacitive acoustic transducer and the power source. The process may then send an acoustic wave into the test sample (operation 1406). This acoustic wave may be sent using a separate device, such as a mechanical transducer, an ordinary electromagnetic acoustic transducer, or a laser. Depending on the particular implementation, the capacitive acoustic transducer also may be configured to send the acoustic wave into the test sample in operation 1406. The process then detects a response (operation 1408). The response is displayed (operation 1410), with the process terminating thereafter.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of advantageous embodiments, the practical application, and to enable others of ordinary skill in the art to understand the disclosure for various embodiments with various modifications as are suited to the particular use contemplated.

What is claimed is:

1. A non-destructive inspection system comprising:
a transducer comprising a capacitor; and
a control unit connected to the transducer and configured to charge the capacitor from a power source to cause an electric field to be produced by the capacitor, to send a command to cause an acoustic source to generate an acoustic wave in a test material, and to detect changes in the electric field after sending the command when the capacitor is positioned such that the electric field extends into the test material.

2. The non-destructive inspection system of claim 1, wherein the control unit is configured to isolate the capacitor from the power source after a charge has built up to a selected amount and while detecting the changes in the electric field after sending the command.

3. The non-destructive inspection system of claim 2, wherein the test material is not a part of the capacitor and the control unit is configured to detect the changes in the electric field generated by the capacitor in response to the acoustic wave propagating in the test material.

4. The non-destructive inspection system of claim 3, wherein the transducer generates the acoustic wave.

5. The non-destructive inspection system of claim 1, wherein the control unit comprises a switch connected to the capacitor and the power source.

6. The non-destructive inspection system of claim 5, wherein the switch is configured to apply power to the capacitor when in a closed state to charge the capacitor to generate the electric field and to isolate the capacitor from the power source when in an open state.

7. The non-destructive inspection system of claim 5, wherein the control unit comprises an oscilloscope.

8. The non-destructive inspection system of claim 5, wherein the transducer comprises the capacitor mounted in a housing.

9. The non-destructive inspection system of claim 8, wherein the housing further comprises the switch.

10. The non-destructive inspection system of claim 8, wherein the capacitor is a surface capacitor.

11. The non-destructive inspection system of claim 8, wherein the capacitor comprises a plurality of concentric rings.

12. The non-destructive inspection system of claim 8, wherein the capacitor has a serpentine structure with interlaced fingers.

13. A method for testing a sample, the method comprising:
supplying power to a capacitor to form a charged capacitor producing an electric field;
positioning the capacitor such that the electric field extends into the sample;
sending an acoustic wave into the sample; and
detecting a response to the acoustic wave by detecting changes in the electric field produced by the charged capacitor in response to the acoustic wave in the sample.

14. The method of claim 13 further comprising:
isolating the charged capacitor from the power to form an isolated charged capacitor.

15. The method of claim 14, wherein the isolating step comprises:
isolating the charged capacitor from the power by opening a switch connecting the capacitor to a power source supplying the power to form the isolated charged capacitor.

16. The method of claim 13, wherein the sending step comprises:
changing a voltage across the capacitor to generate the acoustic wave.

17. The method of claim 13 further comprising:
displaying the response on a display device.

18. The method of claim 13 further comprising:
displaying the response on an oscilloscope.

19. The method of claim 13, wherein the sample is one of a dielectric material, a composite material, or a conducting material.

20. The method of claim 13, wherein the capacitor is mounted in a housing.

* * * * *